US009770319B2

(12) United States Patent
Pinchuk et al.

(10) Patent No.: US 9,770,319 B2
(45) Date of Patent: *Sep. 26, 2017

(54) CLOSED TIP DYNAMIC MICROVALVE PROTECTION DEVICE

(71) Applicant: Surefire Medical, Inc., Westminster, CO (US)

(72) Inventors: Bryan Pinchuk, Denver, CO (US); David Benjamin Jaroch, Arvada, CO (US); James E. Chomas, Denver, CO (US); Aravind Arepally, Atlanta, GA (US)

(73) Assignee: SUREFIRE MEDICAL, INC., Westminster, CO (US)

( * ) Notice: Subject to any disclaimer, the term of this patent is extended or adjusted under 35 U.S.C. 154(b) by 736 days.

This patent is subject to a terminal disclaimer.

(21) Appl. No.: 14/259,293

(22) Filed: Apr. 23, 2014

(65) Prior Publication Data

US 2015/0272716 A1    Oct. 1, 2015

Related U.S. Application Data

(60) Provisional application No. 61/970,202, filed on Mar. 25, 2014.

(51) Int. Cl.
*A61M 29/00* (2006.01)
*A61F 2/01* (2006.01)
(Continued)

(52) U.S. Cl.
CPC ............ *A61F 2/013* (2013.01); *A61B 17/221* (2013.01); *A61B 2017/00867* (2013.01);
(Continued)

(58) Field of Classification Search
CPC ........... A61F 2/01; A61F 2/013; A61M 5/165; A61M 5/16811; A61M 2005/1655
See application file for complete search history.

(56) References Cited

U.S. PATENT DOCUMENTS

| 4,738,740 A | 4/1988 | Pinchuk et al. |
| 5,234,425 A | 8/1993 | Fogarty et al. |

(Continued)

FOREIGN PATENT DOCUMENTS

| EP | 1226795 | 7/2002 |
| EP | 1803423 | 7/2007 |

(Continued)

OTHER PUBLICATIONS

US 7,169,126, 01/2007, Zadno-Azizi (withdrawn)
(Continued)

*Primary Examiner* — Elizabeth Houston
*Assistant Examiner* — Lindsey Bachman
(74) *Attorney, Agent, or Firm* — Gordon & Jacobson, P.C.

(57) ABSTRACT

An endovascular microvalve device for use in a vessel during a therapy procedure includes an outer catheter, an inner catheter displaceable within the outer catheter, and a filter valve coupled to the distal ends of the inner and outer catheters. The valve is constructed of a braid of elongate first filaments coupled together at their proximal ends in a manner that the first filaments are movable relative to each other along their lengths. A filter is provided to the braid formed by electrostatically depositing or spinning polymeric second filaments onto the braided first filaments. The lumen of the inner catheter delivers a therapeutic agent beyond the valve. The device is used to provide a therapy in which a therapeutic agent is infused into an organ.

28 Claims, 8 Drawing Sheets

(51) Int. Cl.
  *A61B 17/221* (2006.01)
  *A61B 17/00* (2006.01)
(52) U.S. Cl.
  CPC ............ *A61B 2017/00871* (2013.01); *A61B 2017/2212* (2013.01); *A61B 2017/2215* (2013.01); *A61F 2002/016* (2013.01); *A61F 2230/0067* (2013.01)

(56) References Cited

U.S. PATENT DOCUMENTS

| | | |
|---|---|---|
| 5,893,869 A | 4/1999 | Barnhart et al. |
| 5,895,399 A | 4/1999 | Barbut et al. |
| 5,910,154 A | 6/1999 | Tsugita et al. |
| 5,911,734 A | 6/1999 | Tsugita et al. |
| 6,00,1118 A | 12/1999 | Daniel et al. |
| 6,010,522 A | 1/2000 | Barbut et al. |
| 6,027,520 A | 2/2000 | Tsugita et al. |
| 6,042,598 A | 3/2000 | Tsugita et al. |
| 6,059,745 A | 5/2000 | Gelbfish |
| 6,152,946 A | 11/2000 | Broome et al. |
| 6,165,200 A | 12/2000 | Tsugita et al. |
| 6,168,579 B1 | 1/2001 | Tsugita |
| 6,179,851 B1 | 1/2001 | Barbut et al. |
| 6,235,044 B1 | 5/2001 | Root et al. |
| 6,258,120 B1 | 7/2001 | McKenzie et al. |
| 6,306,074 B1 | 10/2001 | Waksman et al. |
| 6,306,163 B1 | 10/2001 | Fitz |
| 6,309,399 B1 | 10/2001 | Barbut et al. |
| 6,361,545 B1 | 3/2002 | Macoviak et al. |
| 6,371,969 B1 | 4/2002 | Tsugita et al. |
| 6,371,971 B1 | 4/2002 | Tsugita et al. |
| 6,383,206 B1 | 5/2002 | Gillick et al. |
| 6,395,014 B1 | 5/2002 | Macoviak et al. |
| 6,436,112 B2 | 8/2002 | Wensel et al. |
| 6,443,926 B1 | 9/2002 | Kletschka |
| 6,485,456 B1 | 11/2002 | Kletschka |
| 6,485,502 B2 | 11/2002 | Don Michael et al. |
| 6,499,487 B1 | 12/2002 | McKenzie et al. |
| 6,530,935 B2 | 3/2003 | Wensel et al. |
| 6,533,800 B1 | 3/2003 | Barbut |
| 6,537,294 B1 | 3/2003 | Boyle et al. |
| 6,537,297 B2 | 3/2003 | Tsugita et al. |
| 6,540,722 B1 | 4/2003 | Boyle et al. |
| 6,551,303 B1 | 4/2003 | Van Tassel et al. |
| 6,582,396 B1 | 6/2003 | Parodi |
| 6,589,264 B1 | 7/2003 | Barbut et al. |
| 6,592,546 B1 | 7/2003 | Barbut et al. |
| 6,607,506 B2 | 8/2003 | Kletschka |
| 6,620,148 B1 | 9/2003 | Tsugita |
| 6,635,070 B2 | 10/2003 | Leeflang et al. |
| 6,645,220 B1 | 11/2003 | Huter et al. |
| 6,645,222 B1 | 11/2003 | Parodi et al. |
| 6,645,223 B2 | 11/2003 | Boyle et al. |
| 6,652,555 B1 | 11/2003 | VanTassel et al. |
| 6,652,556 B1 | 11/2003 | VanTassel et al. |
| 6,656,351 B2 | 12/2003 | Boyle |
| 6,673,090 B2 | 1/2004 | Root et al. |
| 6,676,682 B1 | 1/2004 | Tsugita et al. |
| 6,689,150 B1 | 2/2004 | VanTassel et al. |
| 6,692,508 B2 | 2/2004 | Wensel et al. |
| 6,692,509 B2 | 2/2004 | Wensel et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,702,834 B1 | 3/2004 | Boylan et al. |
| 6,706,053 B1 | 3/2004 | Boylan et al. |
| 6,706,055 B2 | 3/2004 | Douk et al. |
| 6,730,108 B2 | 5/2004 | VanTassel et al. |
| 6,746,469 B2 | 6/2004 | Mouw |
| 6,818,006 B2 | 11/2004 | Douk et al. |
| 6,830,579 B2 | 12/2004 | Barbut |
| 6,837,898 B2 | 1/2005 | Boyle et al. |
| 6,855,154 B2 | 2/2005 | Abdel-Gawwad |
| 6,866,677 B2 | 3/2005 | Douk et al. |
| 6,887,258 B2 | 5/2005 | Denison et al. |
| 6,896,690 B1 * | 5/2005 | Lambrecht ............ A61F 2/2427 604/96.01 |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,936,060 B2 | 8/2005 | Hogendijk et al. |
| 6,939,362 B2 | 9/2005 | Boyle et al. |
| 6,964,670 B1 | 11/2005 | Shah et al. |
| 6,964,673 B2 | 11/2005 | Tsugita et al. |
| 6,974,469 B2 | 12/2005 | Broome et al. |
| 6,989,027 B2 | 1/2006 | Allen et al. |
| 7,044,958 B2 | 5/2006 | Douk et al. |
| 7,044,966 B2 | 5/2006 | Svanidze et al. |
| 7,066,946 B2 | 6/2006 | Douk et al. |
| 7,101,396 B2 | 9/2006 | Artof et al. |
| 7,162,303 B2 | 1/2007 | Levin et al. |
| 7,169,164 B2 | 1/2007 | Borillo et al. |
| 7,172,614 B2 | 2/2007 | Boyle et al. |
| 7,172,621 B2 | 2/2007 | Theron |
| 7,214,237 B2 | 5/2007 | Don Michael et al. |
| 7,217,255 B2 | 5/2007 | Boyle et al. |
| 7,223,253 B2 | 5/2007 | Hogendijk |
| 7,232,452 B2 | 6/2007 | Adams et al. |
| 7,232,453 B2 | 6/2007 | Shimon |
| 7,241,304 B2 | 7/2007 | Boyle et al. |
| 7,250,041 B2 | 7/2007 | Chiu et al. |
| 7,252,675 B2 | 8/2007 | Denison et al. |
| 7,279,000 B2 | 10/2007 | Cartier et al. |
| 7,306,575 B2 | 12/2007 | Barbut et al. |
| 7,322,957 B2 | 1/2008 | Kletschka et al. |
| 7,326,226 B2 | 2/2008 | Root et al. |
| 7,331,973 B2 | 2/2008 | Gesswein et al. |
| 7,338,510 B2 | 3/2008 | Boylan et al. |
| 7,344,549 B2 | 3/2008 | Boyle et al. |
| 7,371,249 B2 | 5/2008 | Douk et al. |
| 7,425,215 B2 | 9/2008 | Boyle et al. |
| 7,537,600 B2 | 5/2009 | Eskuri |
| 7,544,202 B2 | 6/2009 | Cartier et al. |
| 7,572,272 B2 | 8/2009 | Denison et al. |
| 7,582,100 B2 | 9/2009 | Johnson et al. |
| 7,585,309 B2 | 9/2009 | Larson |
| 7,591,832 B2 | 9/2009 | Eversull et al. |
| 7,604,650 B2 | 10/2009 | Bergheim |
| 7,647,115 B2 | 1/2010 | Levin et al. |
| 7,653,438 B2 | 1/2010 | Deem et al. |
| 7,833,242 B2 | 11/2010 | Gilson et al. |
| 7,842,084 B2 | 11/2010 | Bicer |
| 7,853,333 B2 | 12/2010 | Demarais |
| 7,873,417 B2 | 1/2011 | Demarais et al. |
| 7,922,691 B2 | 4/2011 | Kletschka et al. |
| 7,937,143 B2 | 5/2011 | Demarais et al. |
| 8,257,384 B2 | 9/2012 | Bates |
| 8,500,775 B2 | 8/2013 | Chomas et al. |
| 8,696,698 B2 | 4/2014 | Chomas et al. |
| 8,696,699 B2 | 4/2014 | Chomas et al. |
| 2002/0161390 A1 | 10/2002 | Mouw |
| 2002/0161394 A1 | 10/2002 | Macoviak et al. |
| 2003/0097114 A1 | 5/2003 | Ouriel et al. |
| 2003/0187474 A1 | 10/2003 | Keegan et al. |
| 2004/0068288 A1 | 4/2004 | Palmer et al. |
| 2004/0181237 A1 * | 9/2004 | Forde ............... A61B 17/12122 606/108 |
| 2004/0220609 A1 | 11/2004 | Douk et al. |
| 2004/0225354 A1 | 11/2004 | Allen et al. |
| 2004/0260333 A1 * | 12/2004 | Dubrul ................. A61B 17/22 606/200 |
| 2005/0010285 A1 | 1/2005 | Lambrecht et al. |
| 2005/0015048 A1 | 1/2005 | Chiu et al. |
| 2005/0015112 A1 | 1/2005 | Cohn et al. |
| 2005/0119688 A1 | 6/2005 | Bergheim |
| 2005/0261759 A1 | 11/2005 | Lambrecht et al. |
| 2006/0167537 A1 | 7/2006 | Larsson et al. |
| 2006/0173490 A1 | 8/2006 | LaFontaine et al. |
| 2007/0106324 A1 | 5/2007 | Garner et al. |
| 2007/0179590 A1 | 8/2007 | Lu et al. |
| 2008/0033341 A1 | 2/2008 | Grad |
| 2008/0039786 A1 | 2/2008 | Epstein et al. |
| 2009/0018498 A1 | 1/2009 | Chiu et al. |

(56) References Cited

U.S. PATENT DOCUMENTS

| | | |
|---|---|---|
| 2009/0076409 A1 | 3/2009 | Wu et al. |
| 2009/0222035 A1 | 9/2009 | Schneiderman |
| 2011/0137399 A1 | 6/2011 | Chomas et al. |
| 2011/0288529 A1 | 11/2011 | Fulton |
| 2012/0116351 A1 | 5/2012 | Chomas et al. |
| 2012/0259206 A1 | 10/2012 | Roberts et al. |
| 2013/0079731 A1 | 3/2013 | Chomas et al. |
| 2013/0226166 A1 | 8/2013 | Chomas et al. |
| 2014/0207178 A1 | 7/2014 | Chomas et al. |

FOREIGN PATENT DOCUMENTS

| | | |
|---|---|---|
| WO | WO 99/16382 | 4/1999 |
| WO | WO 99/44510 | 9/1999 |
| WO | WO 01/41679 | 6/2001 |
| WO | WO 01/45592 | 6/2001 |
| WO | WO 01/49215 | 7/2001 |
| WO | WO 2004/043293 | 5/2004 |

OTHER PUBLICATIONS

Fusion Drug Delivery System-Novel Catheter/Stent Design for Targeted Drug Delivery, Gerschwind & Barnett, Non-Published US provisional patent application filed Sep. 17, 2007.

Fusion Drug Delivery System-Novel Catheter/Stent Design for Targeted Drug Delivery, Gerschwind & Barnett, Non-Published U.S. provisional patent application filed Sep. 17, 2007.

Embolization II, Scientific Session 11, JVIR, Mar. 27, 2012.

Embolization procedure lowers levels of "hunger hormone," leads to weight loss, EurekAlert Public Release, Mar. 7, 2013.

First-In-Man Study of Left Gastric Artery Embolization for Weight Loss, Nicholas Kipshidze et al., ACC.13, E2056, JACC Mar. 12, 2013, vol. 61, Issue 10.

Left Gastric Embolization Leads to Weight Loss, Bariatriac News, Owen Haskins, Dec. 4, 2013.

\* cited by examiner

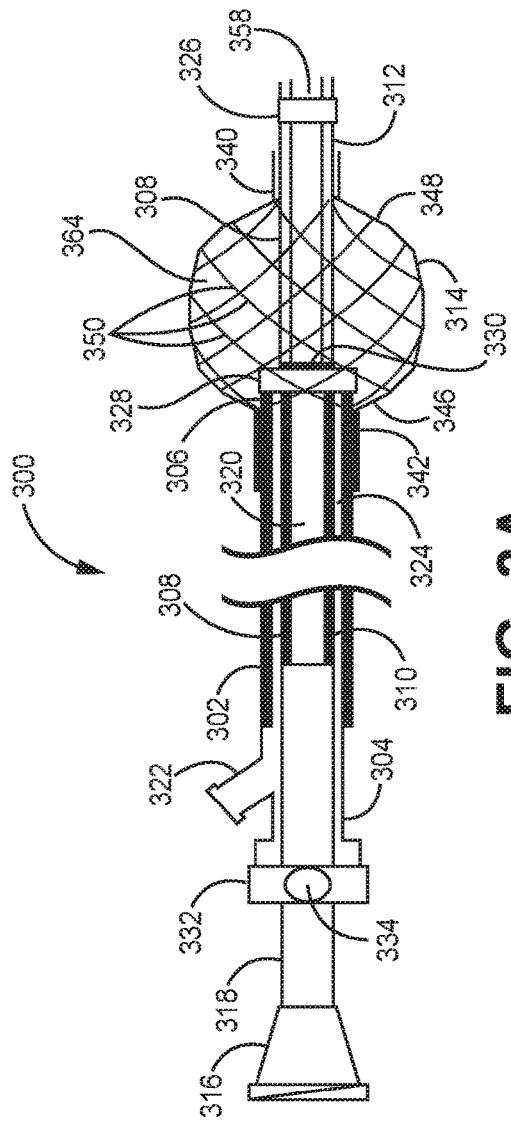
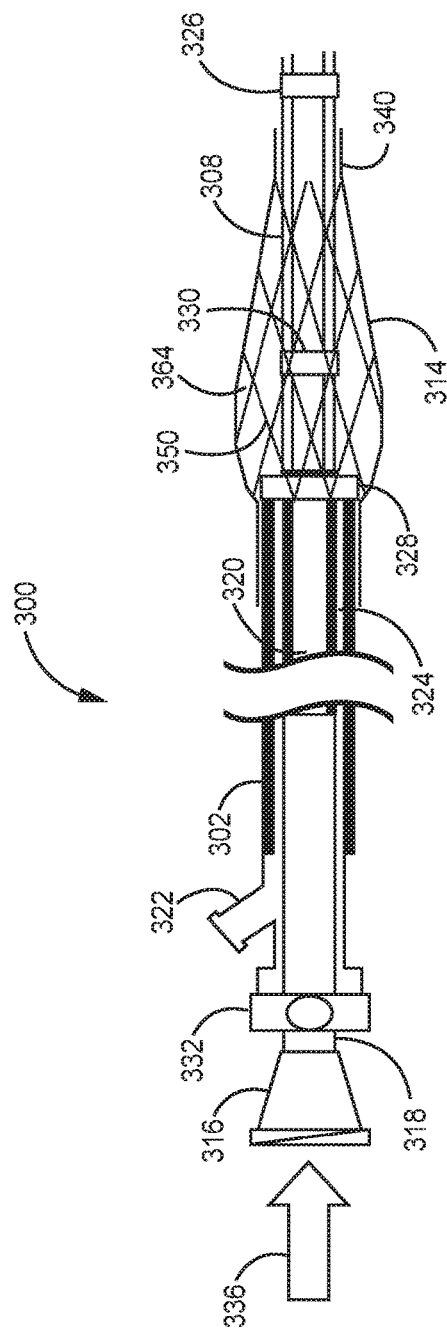
FIG. 3A
FIG. 3B

CLOSED TIP DYNAMIC MICROVALVE PROTECTION DEVICE

CROSS-REFERENCE TO RELATED APPLICATIONS

This application is related to U.S. Pat. No. 8,500,775 and U.S. Ser. No. 12/957,533, filed Dec. 1, 2010, now U.S. Pat. No. 8,696,698, and published as US Pub. No. 20110137399, which are hereby incorporated by reference herein in their entireties.

BACKGROUND OF THE INVENTION

1. Field of Invention

The present invention relates generally to a valve for performing a medical embolizing treatment, and particularly to a valve that increases penetration of a treatment agent into targeted blood vessels and reduces reflux of the treatment agent into non-targeted vessels.

2. State of the Art

Embolization, chemo-embolization, and radio-embolization therapy are often clinically used to treat a range of diseases, such as hypervascular liver tumors, uterine fibroids, secondary cancer metastasis in the liver, pre-operative treatment of hypervascular menangiomas in the brain and bronchial artery embolization for hemoptysis. An embolizing agent may be embodied in different forms, such as beads, liquid, foam, or glue placed into an arterial vasculature. The beads may be uncoated or coated. Where the beads are coated, the coating may be a chemotherapy agent, a radiation agent or other therapeutic agent. When it is desirable to embolize a small blood vessel, small bead sizes (e.g., 10 μm-100 μm) are utilized. When a larger vessel is to be embolized, a larger bead size (e.g., 100 μm-900 μm) is typically chosen.

While embolizing agent therapies which are considered minimally or limited invasive have often provided good results, they have a small incidence of non-targeted embolization which can lead to adverse events and morbidity. Infusion with an infusion microcatheter allows bi-directional flow. That is, the use of a microcatheter to infuse an embolic agent allows blood and the infused embolic agent to move forward in addition to allowing blood and the embolic agent to be pushed backward (reflux). Reflux of a therapeutic agent causes non-target damage to surrounding healthy organs. In interventional oncology embolization procedures, the goal is to bombard a cancer tumor with either radiation or chemotherapy. It is important to maintain forward flow throughout the entire vascular tree in the target organ in order to deliver therapies into the distal vasculature, where the therapy can be most effective. This issue is amplified in hypovascular tumors or in patients who have undergone chemotherapy, where slow flow limits the dose of therapeutic agent delivered and reflux of agents to non-target tissue can happen well before the physician has delivered the desired dose.

The pressure in a vessel at multiple locations in the vascular tree changes during an embolic infusion procedure. Initially, the pressure is high proximally, and decreases over the length of the vessel. Forward flow of therapy occurs when there is a pressure drop. If there is no pressure drop over a length of vessel, therapy does not flow downstream. If there is a higher pressure at one location, such as at the orifice of a catheter, the embolic therapy flows in a direction toward lower pressure. If the pressure generated at the orifice of an infusion catheter is larger than the pressure in the vessel proximal to the catheter orifice, some portion of the infused embolic therapy travels up stream (reflux) into non-target vessels and non-target organs. This phenomenon can happen even in vessels with strong forward flow if the infusion pressure (pressure at the orifice of the catheter) is sufficiently high.

During an embolization procedure, the embolic agents clog distal vessels and block drainage of fluid into the capillary system. This leads to an increase in the pressure in the distal vasculature. With the increased pressure, there is a decrease in the pressure gradient and therefore flow slows or stops in the distal vasculature. Later in the embolization procedure, larger vessels become embolized and the pressure increases proximally until there is a system that effectively has constant pressure throughout the system. The effect is slow flow even in the larger vessels, and distally the embolic agent no longer advances into the target (tumor).

In current clinical practice with an infusion catheter, the physician attempts to infuse embolics with pressure that does not cause reflux. In doing this, the physician slows the infusion rate (and infusion pressure) or stops the infusion completely. The clinical impact of current infusion catheters and techniques is two fold: low doses of the therapeutic embolic is delivered and there is poor distal penetration into the target vessels.

Additionally, reflux can be a time-sensitive phenomenon. Sometimes, reflux occurs as a response to an injection of the embolic agent, where the reflux occurs rapidly (e.g., in the time-scale of milliseconds) in a manner which is too fast for a human operator to respond. Also, reflux can happen momentarily, followed by a temporary resumption of forward flow in the blood vessel, only to be followed by additional reflux.

FIG. 1 shows a conventional (prior art) embolization treatment in the hepatic artery 106. Catheter 101 delivers embolization agents (beads) 102 in a hepatic artery 106, with a goal of embolizing a target organ 103. It is important that the forward flow (direction arrow 107) of blood is maintained during an infusion of embolization agents 102 because the forward flow is used to carry embolization agents 102 deep into the vascular bed of target organ 103.

Embolization agents 102 are continuously injected until reflux of contrast agent is visualized in the distal area of the hepatic artery. Generally, since embolization agents 102 can rarely be visualized directly, a contrast agent may be added to embolization agents 102. The addition of the contrast agent allows for a visualization of the reflux of the contrast agent (shown by arrow 108), which is indicative of the reflux of embolization agents 102. The reflux may, undesirably, cause embolization agents 102 to be delivered into a collateral artery 105, which is proximal to the tip of catheter 101. The presence of embolization agents 102 in collateral artery 105 leads to non-target embolization in a non-target organ 104, which may be the other lobe of the liver, the stomach, small intestine, pancreas, gall bladder, or other organ.

Non-targeted delivery of the embolic agent may have significant unwanted effects on the human body. For example, in liver treatment, non-targeted delivery of the embolic agent may have undesirable impacts on other organs including the stomach and small intestine. In uterine fibroid treatment, the non-targeted delivery of the embolic agent may embolize one or both ovaries leading to loss of menstrual cycle, subtle ovarian damage that may reduce fertility, early onset of menopause and in some cases substantial damage to the ovaries. Other unintended adverse events include unilateral deep buttock pain, buttock necrosis, and uterine necrosis.

Often, interventional radiologists try to reduce the amount and impact of reflux by slowly releasing the embolizing agent and/or by delivering a reduced dosage. The added time, complexity, increased x-ray dose to the patient and physician (longer monitoring of the patient) and potential for reduced efficacy make the slow delivery of embolization agents suboptimal. Also, reducing the dosage often leads to the need for multiple follow-up treatments. Even when the physician tries to reduce the amount of reflux, the local flow conditions at the tip of the catheter change too fast to be controlled by the physician, and therefore rapid momentary reflux conditions can happen throughout infusion.

US Pub. No. 20110137399, previously incorporated herein, describes a microvalve infusion system for infusing an embolic agent to a treatment site in a manner that overcomes many of the issues previously identified with infusion using an infusion catheter alone. Referring to prior art FIGS. 2A and 2B, the microvalve infusion system 200 includes a dynamically adjustably filter valve 202 coupled to the distal end of a delivery catheter 204. The delivery catheter and filter valve extend within an outer catheter 206. The filter valve 202 is naturally spring biased by its construction of filamentary elements 208 to automatically partially expand within a vessel when it is deployed from the outer catheter 206, and is coated with a polymer coating 210 that has a pore size suitable to filter an embolic therapeutic agent. More particularly, the filter valve 202 has an open distal end 212 and is coupled relative to the delivery catheter 204 such that an embolic agent infused through the delivery catheter 204 and out of the distal orifice 214 of the delivery catheter 204 exits within the interior 216 of the filter valve. In view of this construction, upon infusion, an increase in fluid pressure results within the filter valve and causes the filter valve 202 to open, extend across a vessel, and thereby prevent reflux of the infused embolic agent. In addition, as the fluid is pressurized through the delivery catheter and into the filter valve, the downstream pressure in the vessel is increased which facilitates maximum uptake into the target tissue for therapeutically delivered agents. Further, the filter valve is responsive to local pressure about the valve which thereby enables substantially unrestricted forward flow of blood in the vessel, and reduces or stops reflux (regurgitation or backward flow) of embolization agents which are introduced into the blood.

However, the devices in US Pub. No. 20110137399 have certain issues that may not always be advantageous. In various disclosed FIG. 44, the devices shown have a large distal diameter which limits trackability in tortuous branching vasculature. The distal end of the device in a collapsed, undeployed state is defined by the size of an outer catheter 206, which can be significantly larger than the outer diameter delivery catheter 204 that supports the filter valve 202 and significantly larger than the outer diameter of a guidewire (not shown) used to the guide the microvalve to the target location within the vessel. As such, tracking the filter valve into the smaller vascular branches does not have a desired reliability. In addition, once the device is tracked to a treatment location, deployment of the filter valve requires that the frictional force between the filter valve and the outer catheter be overcome. Overcoming such forces can potentially abrade the polymer coating on the filter valve. Improvements to such designs was provided in other figures disclosed in US Pub. No. 20110137399, so that the outer diameter of the distal aspect of the device is reduced in size to in a manner that would facilitate tracking. However, once any of the embodiments of filter valve 202 in US Pub. No. 20110137399 are shown in the open configuration, they assumes the shape of an open frustocone, which allows refluxing therapeutic embolic agent to enter the valve. This may lead to therapeutic agent remaining in the filter valve, particularly under conditions of slow forward flow within the vessel, which potentially could result in incomplete dosing.

SUMMARY OF THE INVENTION

An infusion device is provided that includes an outer catheter, and inner infusion catheter extending through the outer catheter, and a dynamically adjustable filter valve coupled to both of the outer and inner catheters. The filter valve is formed from a naturally spring-biased filamentary construction that is biased to radially expand and has a proximal end and a distal end. The proximal end of the filter valve is coupled to a distal end of the outer catheter, and the distal end of the filter valve is coupled to a distal end of the inner catheter. The filter valve has a closed filtering distal portion, with the proximal and distal portions of the valve separate by the circumference about the maximum diameter of the filter valve. The inner infusion catheter is configured to deliver a therapeutic embolic agent distal of the closed distal portion of the filter valve.

The filter valve can be manually displaced between open and closed configurations by longitudinally displacing the distal end of the inner catheter relative to the distal end of the outer catheter. By displacing the inner catheter distally relative to the outer catheter, the filter valve is moved into a collapsed configuration, suitable for delivery to the treatment site. In the collapsed configuration, the tip is tapered and assumes a form that has excellent trackability over a guidewire to be advanced to a treatment site. To deploy the filter valve, the inner catheter is retracted relative to the outer catheter to cause the filter valve to reconfigure, resulting in radial expansion toward a vessel wall. In addition, the spring-bias of the valve also operates to radial expand the filter valve, particularly when subject to a pressure differential on opposing sides of the filter valve. In a preferred aspect of the invention, the proximal portion of the filter valve has a different radial expansion force than the distal portion of the filter valve. More preferably, the proximal portion has a substantially greater radial expansion force than the distal portion. Once the filter valve is in a deployed open configuration, i.e., with the distal tip in a retracted position relative to the delivery position, the filter valve is dynamically responsive to local pressure about the filter valve. Under the dynamically responsive operation, substantially unrestricted forward flow of blood in the vessel is permitted, while backflow is prevented to stop reflux of the therapeutic agent within the vessel.

Upon retrieval of the infusion device at the end of the procedure the inner catheter can be further retracted into the outer catheter (such that the filter valve is substantially inverted and received within the outer catheter) to thereby capture and contain any therapeutic agent remaining on the filter valve.

BRIEF DESCRIPTION OF DRAWINGS

Prior art

Prior art

FIGS. 3A and 3B are schematic figures of an exemplary embodiment of a therapeutic filter valve device in a deployed state and an undeployed state, respectively.

DETAILED DESCRIPTION OF THE PREFERRED EMBODIMENTS

Figure 1:
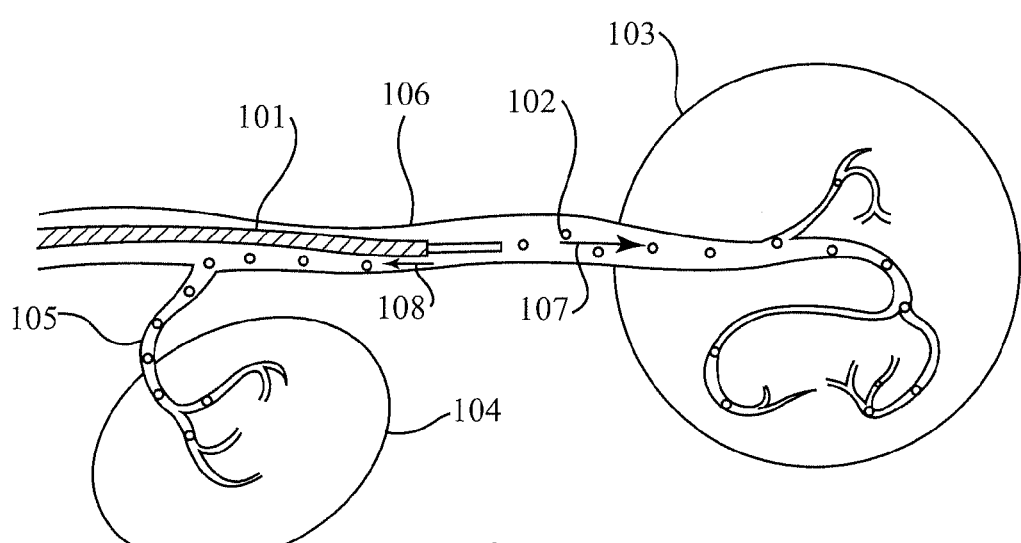
FIG. 1 shows a conventional embolizing catheter in a hepatic artery with embolizing agent refluxing into a non-targeted organ.
Figure 2A:
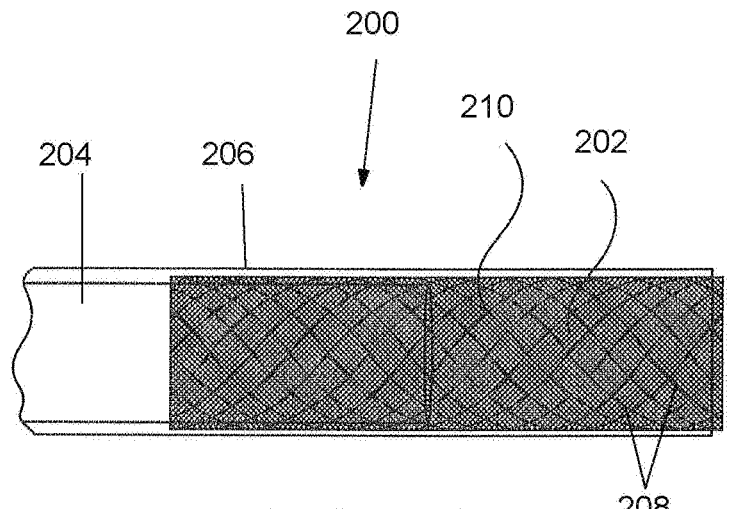
FIGS. 2A and 2B are schematic figures of a prior art filter valve device shown in an undeployed configuration and a deployed configuration, respectively.
Figure 2B:
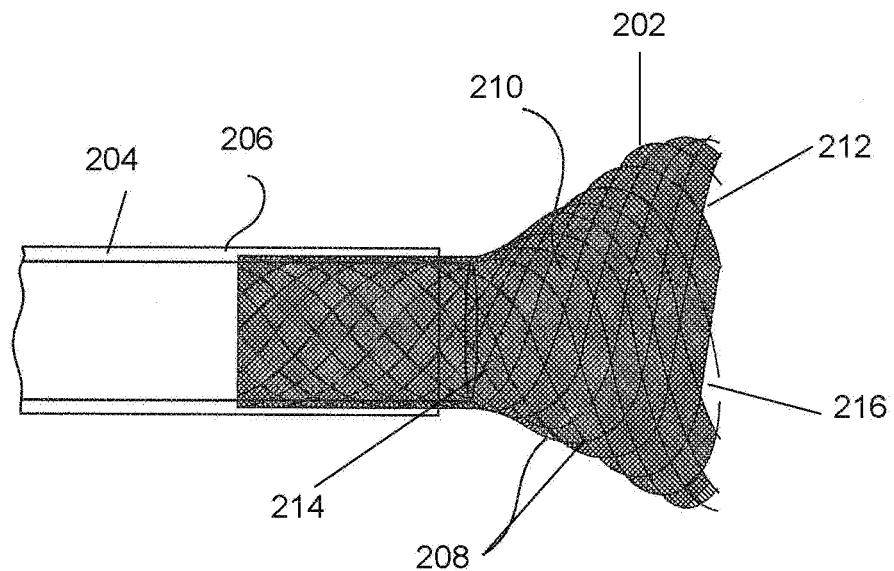

With reference to the human body and components of the devices and systems described herein which are intended to be hand-operated by a user, the terms "proximal" and "distal" are defined in reference to the user's hand, with the term "proximal" being closer to the user's hand, and the term "distal" being further from the user's hand, unless alternate definitions are specifically provided.

A first exemplary embodiment of a microvalve device 300 according to the invention is seen in FIGS. 3A and 3B. It is noted that respective portions of the system illustrated in FIGS. 3A and 3B are not shown proportional to their intended size, but rather that the distal portion is illustrated significantly enlarged for purposes of explanation. As shown in FIG. 3A, the device 300 includes a flexible outer catheter 302 having a proximal end 304 and a distal end 306, a flexible inner delivery catheter 308 extending through and longitudinally displaceable relative to the outer catheter 304 and having a proximal end 310 and a distal end 312, and a filter valve 314 coupled to the distal ends 306, 312 of the outer and inner catheters 304, 308. The proximal end 310 of the inner catheter is preferably mounted to a hub 316 with a rigid tubular coupling member 318. The tubular coupling member 318 is preferably a stainless steel hypotube or similar structure. An infusion lumen 320 is defined from the hub 316 through to the distal end 312 of the inner catheter and is adapted for delivery of a therapeutic agent, including an embolizing agent, from outside the body of the patient (not shown) to a target vessel (artery or vein) in the patient.

The proximal end 304 of the outer catheter 302 preferably includes a side arm port 322 that is in fluid communication with an annular space 324 formed between the inner and outer catheters 304, 308 and extending into the interior of the filter valve 314, and to flush the annular space 324 of the filter valve. Flushing such space, such as with a lubricant, including saline, operates to reduce friction between the inner and outer catheter to facilitate longitudinal movement therebetween.

A first radio-opaque marker band 326 is provided at the distal end 312 of the inner catheter 308, and a second preferably larger radio-opaque marker band 328 is provided at the distal end 306 of the outer catheter 302. A third radio-opaque marker band 330 is provided to the inner catheter 308 in a defined positional relationship relative to the second marker band 328. By example, the third marker band 330 may be co-longitudinally positioned with the second marker band 328 when the inner and outer catheters 302, 308 are positioned to cause the filter valve 314 to be in a deployed configuration, as shown in FIG. 3A and discussed below. FIG. 3B illustrates the microvalve device 300 in a non-deployed configuration and relative positioning of the three marker bands 326, 328, 330. During use of the device 300, the in vivo relative positions of the marker bands 326, 328, 330, viewed fluoroscopically, indicates the displacement of the distal ends 306, 312 of the inner and outer catheters and the consequent configuration of the filter valve, as discussed in more detail below.

A handle 332 is optionally provided at or adjacent the proximal ends of the inner and outer catheters 302, 308 (including tubular coupling member 318) to controllably longitudinally displace the inner and outer catheters relative to each other. By way of example only, the handle 322 may include a standard slider assembly, e.g., in the form of a spool and shaft, that converts manual longitudinal movement of the user into a desired and controlled longitudinal displacement between the inner and outer catheters. As yet another alternative, the handle may include a rotation knob 334 connected to a lead screw that converts manual user rotational movement into a desired and controlled longitudinal displacement between the distal ends of the inner and outer catheters, such as shown by arrow 336 (FIG. 3B).

The inner catheter 308 is between two and eight feet long, and has an outer diameter of between 0.67 mm and 3 mm (corresponding to catheter sizes 2 French to 9 French), and is made from a liner made of fluorinated polymer such as polytetrafluoroethylene (PTFE) or fluorinated ethylene propylene (FEP), a braid made of metal such as stainless steel or titanium, or a polymer such as polyethylene terephthalate (PET) or liquid crystal polymer, and an outer coating made of a polyether block amide thermoplastic elastomeric resin such as PEBAX®, polyurethane, polyamide, copolymers of polyamide, polyester, copolymers of polyester, fluorinated polymers, such as PTFE, FEP, polyimides, polycarbonate or any other suitable material, or any other standard or specialty material used in making catheters used in the bloodstream.

The outer catheter 302 is comprised of polyurethane, polyamide, copolymers of polyamide, polyester, copolymers of polyester, fluorinated polymers, such as PTFE, FEP, polyimides, polycarbonate or any other suitable material. The outer catheter 302 may also contain a braid composed of metal such as stainless steel or titanium, or a polymer such as PET or liquid crystal polymer, or any other suitable material. The wall thickness of the outer catheter 302 is preferably in the range of 0.05 mm to 0.25 mm with a more preferred thickness of 0.1 mm-0.15 mm.

The distal end 340 of the filter valve 314 is fused or otherwise fixedly coupled (both longitudinally and rotationally fixed) adjacent, but preferably slightly proximally displaced from, the distal end 312 of the inner catheter 308, and the proximal end 342 of the filter valve is fused or otherwise coupled at or adjacent the distal end 306 of the outer catheter 302.

The filter valve 314 is composed of one, two, or more metal (e.g., stainless steel or Nitinol) or polymer filaments 350, which form a substantially closed shape when deployed and not subject to outside forces. Where polymeric filaments are utilized, the filaments 350 may be composed of PET, polyethylene-napthalate (PEN), liquid crystal polymer, fluorinated polymers, nylon, polyamide or any other suitable polymer. If desired, when polymeric filaments are utilized, one or more metal filaments may be utilized in conjunction with the polymeric filaments. According to one aspect of the invention, where a metal filament is utilized, it may be of radio-opaque material to facilitate tracking the filter valve 314 and its configuration within the body. In a deployed, expanded diameter configuration, the filter valve 314 is capable of being modified in shape by fluid forces. It is preferred that the filaments 350 not be bonded to each between their ends so to enable the valve to rapidly automatically open and close in response to dynamic flow conditions. The multiple filaments 350 of the filter valve are preferably braided and can move relative to each other between their ends. As discussed hereinafter, the filaments are spring biased (i.e., they have "shape memory") to assume a desired crossing angle relative to each other so that the valve can self-assume a desired shape.

Figure 4:
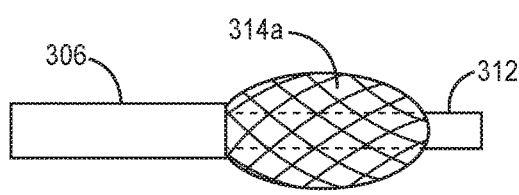
FIG. 4 is a schematic view of a shape of the distal end of a deployed filter valve device.
Figure 5:
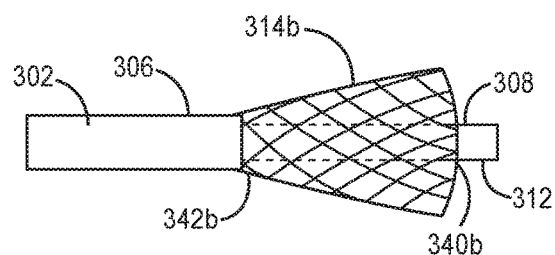
FIG. 5 is a schematic view of another shape of the distal end of a deployed filter valve device.

In the device shown in FIG. 3A, the assumed shape in substantially spherical, though as described hereinafter the shape can be substantially frustoconical. (For purposes herein the term "substantially spherical" should be understood to include not only a sphere, but a generally rounded shape including a spherical portion or a rounded oblong shape 314a, such as shown in FIG. 4, or a portion thereof. For purposes herein the term "substantially frustoconical" should be understood to include not only a generally truncated cone, but a truncated hyperboloid, a truncated paraboloid, and any other shape 314b which starts from a circular proximal end 342b at the distal end 306 of the outer catheter 302 and diverges therefrom and returns to close back down at the distal end 340b of the filter valve adjacent the distal end 312 of the inner catheter 308, as shown in FIG. 5). In all embodiments, the shape of the filter valve 314 is closed down at or adjacent the respective ends 306, 312 of the outer and inner catheters 302, 308, and can be defined by a proximal hemispherical portion 346 and a distal hemispherical portion 348, or two conical portions, or a proximal spherical portion and a distal conical portion, or a proximal conical portion and a distal spherical portion, or any of the preceding with an intervening shaped portion therebetween, which are joined together at preferably the largest diameter ends of the respective portions. As such, it is appreciated that the proximal and distal portions 346, 348 of the filter valve 314 are not required to be longitudinally symmetrical, and may be asymmetrical, in construction, which is apparent in the non-deployed configuration of the filter valve 314 shown in FIG. 3B. The joined proximal and distal portions each may have filaments oriented at a different braid angle, discussed below. In addition, the proximal and distal portions may be joined mechanically via the ends of the filaments, or by the filter material, which is discussed in more detail below.

Figure 6A:
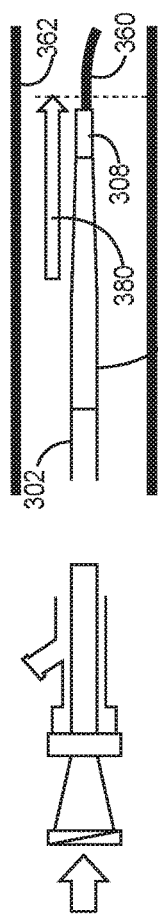
FIG. 6A-6D are broken schematic diagrams of the exemplary embodiment of the filter valve device of FIGS. 3A and 3B, in use, with the distal end of the device illustrated positioned within a vessel.

The filter valve 314 is designed to be manually reconfigured between non-deployed and deployed configurations by movement of the inner and outer catheters relative to each other, wherein in each of the non-deployed and deployed configurations the distal end of the filter valve extends outside and distally of the distal end of the outer catheter. As shown in FIGS. 3B and 6A, in the non-deployed configuration, the filter valve 314 is provided with a smaller maximum diameter suitable for tracking the device over a guidewire 360 (FIG. 6A) through the vessels 362 to a treatment site. The inner catheter 308 is displaced distally relatively to the outer catheter 302 (in the direction of arrow 380) to stretch or otherwise present the filter valve in an elongate configuration having a tapered tip which facilitates trackability over the guidewire 360. In this collapsed, non-deployed configuration, the inner catheter 308 is preferably pushed as distal as possible relative to the outer catheter 302. In a preferred embodiment, the non-deployed elongated configuration of the filter valve tapers distally over at least 50%, and preferably at least 75%, of its length.

Figure 6B:
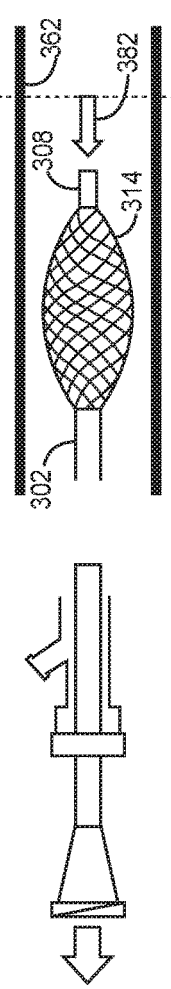
Figure 6C:
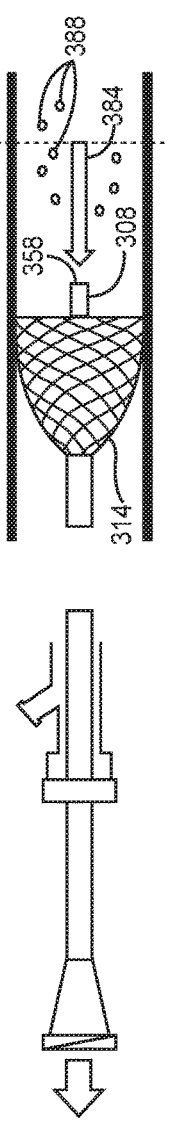
Figure 7:
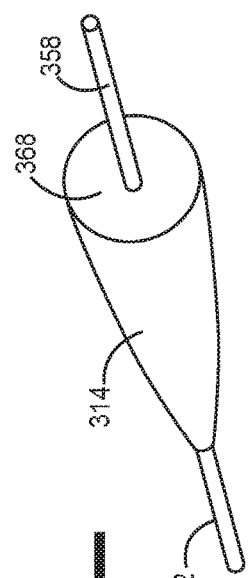
FIG. 7 is perspective distal end photographic view of the distal end of the filter valve device in a deployed configuration.

Then, referring to FIG. 6B, once the filter valve is positioned at the treatment site in the vessel 362, the inner catheter 308 can be refracted relative to the outer catheter 302 (in the direction of arrow 382) to expand the filter valve 314 and cause the filter valve to assume (initially) a partially deployed configuration within the vessel in which the filter valve does not seal against the vessel wall 362. Alternatively or thereafter, as shown in FIG. 6C, the inner catheter 308 can be further retracted relative to the outer catheter 302 (as indicated by arrow 384) to more fully expand the filter valve 314 to seal against the vessel wall 362. This configuration of the filter valve 314 is also shown in FIG. 7. When retracted into the configuration shown in FIG. 6B, the proximal end of the filter valve 314 forms a distal facing plane or concave surface 368 (with it being understood that in the non-deployed configuration of the filter valve presents a distal facing convex or convexly conical surface), while the proximal facing surface remains unmodified in shape and is generally a smooth convex surface. Then, with the filter valve deployed, embolization agents 388 are delivered under pressure distally through and out of the inner catheter, distal of the filter valve, and into the vessel. Delivery of the embolization agents in this manner will result in a downstream pressure change that initially causes higher pressure distal of the filter valve than upstream of the filter valve rapidly sealing to the vessel wall and directing all infusion pressure downstream. In its open position, the filter valve stops embolization agents from traveling upstream past the filter valve in a proximal 'reflux' direction. In addition, because the filter valve is a closed shape and delivers the embolic distal of the filter valve, 100% of the dose delivered is provided to the patient; i.e., without the potential for any of the dose to remain within the filter valve. Further, the shape of the proximal surface of the deployed filter valve presents reduced resistance to blood passing the filter valve in the downstream direction, but presents a distal facing surface at a different orientation and one that is substantially perpendicular to the vessel wall and has significant resistance to flow in the upstream direction so as to prevent reflux.

Figure 8A:
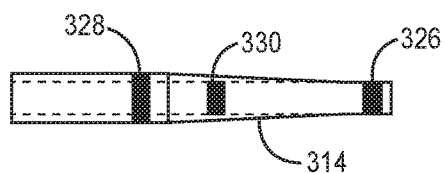
FIGS. 8A-8C are schematic views of the distal end of the filter valve device in non-deployed and deployed configurations, indicating the respective positions of radio-opaque marker bands.
Figure 8B:
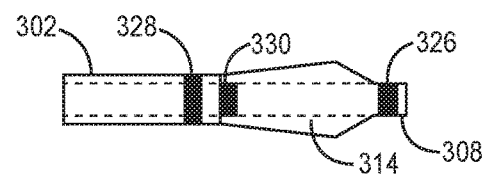
Figure 8C:
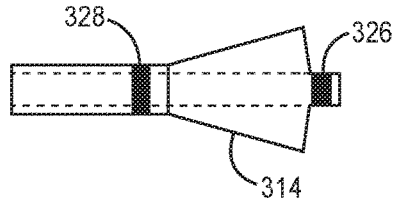

Turning now to FIGS. 8A-8C, the above described radio-opaque first, second and third marker bands 326, 328, 330 facilitate determining the in vivo configuration of the filter valve. Referring to FIG. 8A, by way of example only, when the three marker bands 326, 328, 330 are shown spaced apart, the filter valve 314 can be indicated to be in the non-deployed configuration. In FIG. 8B, with the third marker band 330 offset substantially closer to the second marker band 328, the filter valve 314 can be indicated to be in a partially deployed configuration, with the inner catheter 308 somewhat retracted relative to the outer catheter 302. FIG. 8C, under fluoroscopy, would show two bands 326, 328, with the second marker band hiding the third marker band 330 (FIG. 8B), indicating the fully deployed configuration. Other relative relationships of the marker bands are possible to provided fluoroscopic indicia with respect to the state of the filter valve.

Figure 9:
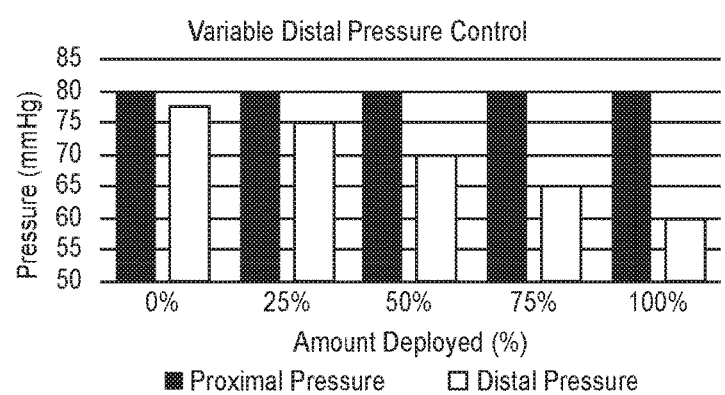
FIG. 9 is a graph indicating the variable pressure control distal of the filter valve device.
Figure 10A:
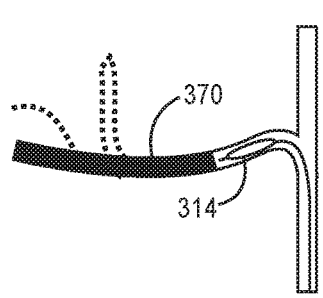
FIGS. 10A-10C are schematic views of the deployed filter valve device, using variable pressure control to selectively infuse primary and branch vessels.
Figure 10B:
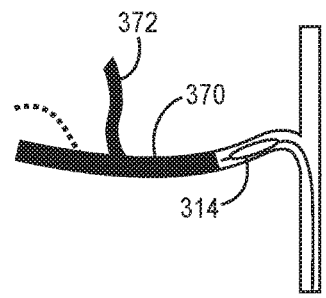
Figure 10C:
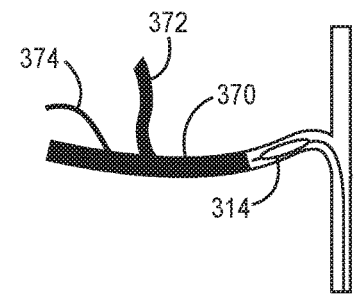

Referring now to FIG. 9, when the filter valve is advanced to a treatment site within a vessel in the non-deployed configuration, a very small pressure differential (e.g., 2.5 mmHg) is generated between the proximal and distal sides of the filter valve. When the filter valve is partially opened, i.e., deployed but not extending to the vessel wall (indicated in FIG. 9 as deployed '25%'), a small but relatively larger pressure differential (e.g., 5 mmHg) is generated between the proximal and distal sides of the filter valve. When the filter valve is fully opened so that the filter valve contacts the vessel wall (indicated deployed '50%'), a larger pressure differential (e.g., 10 mmHg) is generated between the proximal and distal sides of the filter valve. When the filter valve is fully opened and an infusate is infused through the orifice of the inner catheter to a location distal of the filter valve, a significantly larger pressure differential (e.g., 10-20 mmHg) is generated between the proximal and distal sides of the filter valve. Referring to FIGS. 10A-10C, the range of generated pressure differentials can be used to selectively treat vessels of different diameter downstream of the filter valve. Referring to FIG. 10A, with significant generated flow and a pressure drop between the proximal and distal sides of the filter valve, the infusate is directed downstream to at least the largest target vessel 370. Then, referring to FIG. 10B, by generating an increase in pressure differential by raising the fluid pressure of the infusate, additional smaller target branch vessels 372 resistant to the perfusion at the initial infusate pressure are perfused. Finally, referring to FIG. 10C, by increasing the pressure differential again, even smaller target branch vessels 374 can be perfused. Similarly, to the extent that treatment is intended to be limited to only certain vessels, the distal pressure can be limit to below that required to perfuse the smaller vessels.

Figure 6D:
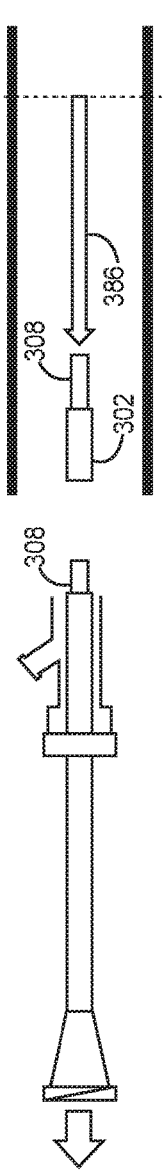

According to one aspect of the invention, the valve is preferably capable of being configured into its closed position after the embolization treatment procedure is completed for removal from the patient. In one configuration for post-treatment removal from the patient, the valve is simply withdrawn in the deployed configuration. In another configuration, the inner catheter 308 is further retracted relative to the outer catheter 302 to invert a portion or all of the distal filter valve 348 into the proximal valve 346 to contain embolic agent that may potentially remain on the filter valve after the treatment. In yet another configuration, as shown in FIG. 6D, the inner catheter is even further refracted relative to the outer catheter (in the direction of arrow 386) to invert the entire filter valve 314 into the outer catheter 302 to fully contain any embolic agent that may potentially remain on the filter valve after the treatment.

Now, as discussed in previously incorporated US Pub. No. 20110137399, three parameters help define the performance and nature of the deployed filter valve: the radial (outward) force of the valve, the time constant over which the valve changes condition from closed to open, and the pore size of the filter valve.

In a preferred embodiment, the filter valve expands into the deployed configuration when, first, the inner and outer catheter are displaced to move the distal end of the filter valve relative to the proximal end of the filter valve and thereby shorten and expand the valve into the deployed configuration. However, once deployed, the filter valve fully expands to the vessel wall (i.e., reaches an open condition) when the pressure at the distal orifice of the inner catheter is greater than the blood pressure. The filter valve is also in a deployed but closed condition (with filter valve retracted from the vessel wall) when blood is flowing upstream, or in a proximal to distal direction, with pressure greater than the pressure at the inner catheter orifice. In addition, when the radial force of expansion on the filter valve (i.e., the expansion force of the filter valve itself in addition to the force of pressure in the distal vessel over the distal surface area of the valve) is greater than the radial force of compression on the filter valve (i.e., force of pressure in the proximal vessel over the proximal surface area of the filter valve), the filter valve fully expands so that the valve assumes the open configuration. Thus, the radial force of expansion of the filter valve is chosen to be low (as described in more detail below) so that normal blood flow in the downstream distal direction will prevent the deployed filter valve from reaching the open condition. This low expansion force is different than the expansion forces of prior art stents, stent grafts, distal protection filters and other vascular devices, which have significantly higher radial forces of expansion. It is appreciated that expansion force is sufficiently low that it will not cause the inner catheter to move relative to the outer catheter; such relative movement is preferably effected only by the user of the device.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0}$$

$$K_2 = \frac{2\cos^2\beta_0}{D_0}$$

$$K_3 = \frac{D_0}{\cos\beta_0}$$

and I and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), stent diameter ($D_0$), and number of filaments (n) impact the radial force of the braided valve.

In one examplar embodiment, the filter valve 314 is composed of twenty-four polyethylene terephthalate (PET) filaments 350, each having a diameter of 0.1 mm and pre-formed to an 8 mm diameter mandrel and a braid angle of 130° (i.e., the filaments are spring-biased or have a shape memory to assume an angle of 130° relative to each other when the valve assumes a fully deployed state and opens in a frustoconical configuration). The filaments 350 preferably have a Young's modulus greater than 200 MPa, and the filter valve 314 preferably has a radial force of less than 40 mN in the fully deployed position (i.e., where the filaments assume their shape memory). More preferably, the filter valve 314 has a radial force in the fully deployed position of less than 20 mN, and even more preferably the filter valve has a radial force of approximately 10 mN (where the term "approximately" as used herein is defined to mean±20%) in the deployed position.

In one embodiment, when subject to an infusion pressure at the distal orifice 358 of the inner catheter, the filter valve 314 moves between deployed positions allowing downstream fluid passage (closed) and preventing fluid passage (open) in a static fluid (e.g., glycerin) having a viscosity approximately equal to the viscosity of blood (i.e., approximately 3.2 cP) in 0.067 second. For purposes herein, the time it takes to move from the closed position to the open position in a static fluid is called the "time constant". According to another aspect of the invention, the filter valve 314 is arranged such that the time constant of the filter valve 314 in a fluid having the viscosity of blood is between 0.01 seconds and 1.00 seconds. More preferably, the filter valve 314 is arranged such that the time constant of the filter valve in a fluid having the viscosity of blood is between 0.05 and 0.50 seconds. The time constant of the filter valve 314 may be adjusted by changing one or more of the parameters described above (e.g., the number of filaments, the modulus of elasticity of the filaments, the diameter of the filaments, etc.).

According to one aspect of the invention, the deployed filter valve opens and closes sufficiently quickly to achieve high capture efficiency of embolic agents in the presence of rapidly changing pressure conditions. More particularly, as shown in FIG. 6C, with the inner and outer catheter displaced to open the filter valve to the vessel wall 362, when pressure at the distal orifice 358 of the inner catheter 308 (distal of the deployed filter valve 314) increases higher than the pressure in the blood vessel 362, the seal between the periphery of the filter valve and the vessel wall is increased, thus blocking refluxing embolics. It is important to note that pressure is communicated throughout the vasculature at the speed of sound in blood (1540 m/s) and that the valve opens and closes in in response to pressure changes within the blood vessel. Since the expandable filter valve responds to pressure changes, it reacts far faster than the flow rates of embolics in the blood (0.1 m/s) thereby preventing reflux of any embolics.

As will be appreciated by those skilled in the art, the braid geometry and material properties of the filaments 350 are intimately related to the radial force and time constant of the filter valve. Since, according to one aspect of the invention, the filter valve is useful in a variety of vessels of different diameters and flow conditions, each implementation can have a unique optimization. By way of example only, in one embodiment, the filter valve 314 has ten filaments 350, whereas in another embodiment, the filter valve has forty filaments 350. Any suitable number of filaments can be used. Preferably, the diameter of the filaments are chosen in the range of 0.025 mm to 0.127 mm, although other diameters may be utilized. Preferably, the pitch angle (i.e., the crossing angle assumed by the braided filaments in the fully open deployed position) is chosen in the range of 100° to 150°, although other pitch angles may be used. Preferably, the Young's modulus of the filament is at least 100 MPa, and more preferably at least 200 MPa.

The filter valve 314 is chosen to have a pore size which is small enough to capture (filter) embolic agents in the blood stream as the blood passes through the filter valve. Where large embolic agents (e.g., 500 μm) are utilized, it may be possible for the filaments alone to act directly as a filter to prevent embolic agents from passing through the valve (provided the filaments present pores of less than, e.g., 500 μm). Alternatively, a coating 364 is preferably added to the filaments 350, and more preferably to the formed braid structure, to provide the filter function. Such a separate polymeric filter is particularly useful where smaller embolic agents are utilized. The polymeric filter can be placed onto the braid structure by spraying, spinning, electrospinning, bonding with an adhesive, thermally fusing, mechanically capturing the braid, melt bonding, dip coating, or any other desired method. The polymeric coating 364 can either be a material with pores such as ePTFE, a solid material that has pores added such as polyurethane with laser drilled holes, or the filter coating can be a web of very thin filaments that are laid onto the braid. Where the coating 364 is a web of thin filaments, the characteristic pore size of the filter can be determined by attempting to pass beads of different diameters through the filter and finding which diameter beads are capable of passing through the filter in large quantities. The very thin filaments can be spun onto a rotating mandrel according to U.S. Pat. No. 4,738,740 with the aid of an electrostatic field or in the absence of an electrostatic field or both. The filter thus formed can be adhered to the braid structure with an adhesive or the braid can be placed on the mandrel and the filter spun over it, or under it, or both over and under the braid to essentially capture it. The filter 364 can have some pores formed from spraying or electrospinning and then a secondary step where pores are laser drilled or formed by a secondary operation. In the preferred embodiment a material capable of being electrostatically deposited or spun is used to form a filter on the braid, with the preferred material being capable of bonding to itself. The filter may be made of polyurethane, pellethane, polyolefin, polyester, fluoropolymers, acrylic polymers, acrylates, polycarbonates, or other suitable material. The polymer is spun onto the braid in a wet state, and therefore it is desirable that the polymer be soluble in a solvent. In the preferred embodiment, the filter is formed from polyurethane which is soluble in dimethylacetamide. The polymer material is spun onto the braid in a liquid state, with a preferred concentration of 5-10% solids for an electrostatic spin process and 15-25% solids for a wet spin process.

According to one aspect of the invention, the filter coating 364 has a characteristic pore size between 10 μm and 500 μm. More preferably, the filter has a characteristic pore size between 15 μm and 100 μm. Even more preferably, the filter has a characteristic pore size of less than 40 μm and more preferably between 20 μm and 40 μm. Most desirably, the filter is provided with a characteristic pore size that will permit pressurized blood and contrast agent to pass therethrough while blocking passage of embolizing agent therethrough. By allowing regurgitating blood and contrast agent to pass through the filter in a direction from distal the valve toward the proximal end of the valve, the contrast agent may be used to indicate when the target site is fully embolized and can serve to identify a clinical endpoint of the embolization procedure. Therefore, according to one aspect of the invention, the valve allows the reflux of the contrast agent as an indicator of the clinical endpoint while preventing the reflux of the embolization agents at the same time. In addition, by allowing blood to flow back through the filter material, even at a relatively slow rate, backpressure on the distal side of the valve can be alleviated.

The filter valve is also preferably provided with a hydrophilic coating, hydrophobic coating, or other coating that affects how proteins within blood adhere to the filter and specifically within the pores of the filter. More specifically, the coating is resistant to adhesion of blood proteins. One coating that has been used successfully is ANTI-FOG COATING 7-TS-13 available from Hydromer, Inc. of Branchburg, N.J., which can be applied to the filter by, e.g., dipping, spraying, roll or flow coating.

By appropriate design of the pore size and use of an appropriate coating, proteins in the blood will almost immediately fill the pores during use. The proteins on the coated porous filter operate as a pressure safety valve, such that the pores are filled with the proteins when subject to an initial fluid pressure greater than the blood vessel pressure, but the proteins are displaced from the pores and the pores are opened to blood flow at higher pressures such as a designated threshold pressure. The designated threshold pressure is determined to prevent damage to the tissue and organs, and injury to the patient. Thus, this system allows a pressure greater than the vessel pressure while limiting very high pressures which may be unsafe to the patient. As such, the system provides pressure regulation which is not possible with other occlusive devices, including balloons. Notwithstanding the advantage of the above, it is not a requirement of the invention that the filter be constructed to allow either blood or contrast agent to pass through in the upstream 'reflux' direction under any determined pressure.

It is recognized that in the open state, proteins in the blood may rapidly fill the pores of the filter valve. However, as discussed above, should a threshold pressure be reached, the filter valve is designed to permit the blood to reflux through the pores of the filter valve while still blocking the passage of the embolic agent. An exemplar threshold pressure is 180 mmHg on the distal surface of the filter valve, although the device can be designed to accommodate other threshold pressures. Such can be effected, at least in part, by the use of an appropriate coating on the filter that facilitates removal of the blood proteins from within the filter pores when subject to threshold pressure. This prevents the vessel in which the device is inserted from being subject to a pressure that could otherwise result in damage. Nevertheless, it is not necessary that blood and contrast agent be permitted to reflux through the valve.

In a preferred embodiment, the filter coating 350 is preferably provided as a homogenous coating of filaments, with the proximal and distal portions 346, 348 of the filter valve 314 having a uniform coating construct. As the filter valve 314 is provided in the form of a closed shape, with its proximal end 346 fused to the outer catheter 302, and its distal end 348 fused to the inner catheter 308, it is appreciated that any fluid or agent passing from the vessel and through the filter must through two similar layers of the filter; i.e., a layer at the proximal side of the filter valve and a layer at the distal side of the filter valve.

In accord with one aspect of the invention, the filter valve has a different radial force at its proximal portion relative to its distal portion. This difference in radial force to enable behavior that is dependent on the direction of the flow (i.e. the valve behavior). It is preferred that the distal portion have lower radial force than the proximal portion, as described in FIGS. 11-16, as follows.

Figure 11:
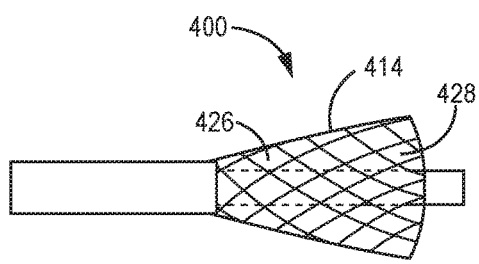
FIG. 11 is a schematic distal end view of an alternate coating construct for the filter valve device.

Turning now to FIG. 11, another filter valve 414 at the distal end of a microvalve device 400 is shown. The filter valve 414 includes a heterogeneous filter coating in which the entire filter valve is coated. The coating 450 includes smaller pores at the proximal portion 426 of the filter valve, and larger pores at the distal portion 428. By way of example only, the smaller pores can be on the order to one micron, whereas the larger pores can be on the order to 30 microns. The difference in pore size may be provided by placing more of the same filamentary coating at the proximal portion and relatively less at the distal portion to provide a greater radial force in the proximal portion compared to the distal portion. The difference in radial force allows the filter valve to have different performance in forward flow compared to backflow. In forward flow, the device remains in a conical shape allowing fluid around it. In backflow, the very weak structure collapses inward, allowing fluid pressure to seal the device against the vessel wall and reducing backflow.

Figure 12:
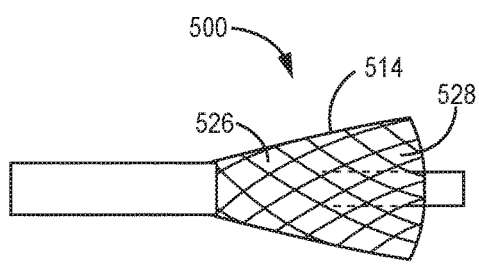
FIG. 12 is a schematic distal end view of another coating construct for the filter valve device.

Referring now to FIG. 12, yet another embodiment of a filter valve 514 at the distal end of a microvalve device 500 is shown. The filter valve 514 includes a heterogenous filter coating in which the entire filter valve is coated. The coating 550 includes a non-porous membrane provided at the proximal portion 526 of the filter valve, and a porous filamentary coating at the distal portion 528. The non-porous membrane does not allow flow through the membrane, thus increasing the antegrade flow around the device in forward flow. The porous membrane on the distal portion allows flow through the device, which expands the filter valve to the wall in backflow to more effectively block embolic agents from flowing backward.

Figure 13:
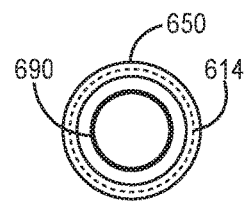
FIG. 13 is a schematic distal end view of yet another alternate coating construct for the filter valve device.

Turning now to FIG. 13, another embodiment of a filter valve 614 is shown. The filter valve has a non-porous membrane coating 690 at its inner surface 692 of the proximal portion, and a filter coating 650 on the outer surface of at least the distal portion of the filter valve, and preferably the entire filter valve. The combination of a non-porous membrane and porous membrane on the proximal portion both increases antegrade flow and radial strength in forward flow while the porous membrane on the distal portion reduces radial strength and allows flow into the filter valve in back flow to seal the vessel and block the reflux of embolic agents.

Figure 14:
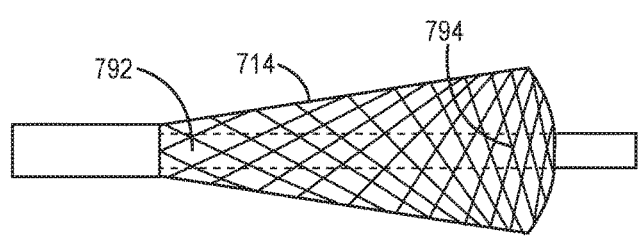
FIG. 14 is a schematic distal end view of a braid angle construct for any of the filter valve devices.

Referring now to FIG. 14, another embodiment of the filter valve 714 is shown. The filter valve has a construction with a variable braid angle; i.e., with different braid angles at different portions of the filter valve. In the illustrated embodiment, the braid angle is lower at the proximal end and higher at the distal end. The lower braid angle, e.g., at 792, is preferably in the range of 60-90°, and the higher braid angle, e.g., at 794, is preferably greater than 110°. Lower braid angle has a greater stiffness than lower braid angle, again providing a different operating behavior in forward flow compared to backward flow. The variable braid angle aspect of the device can be used in conjunction with any other embodiment described herein.

Figure 15:
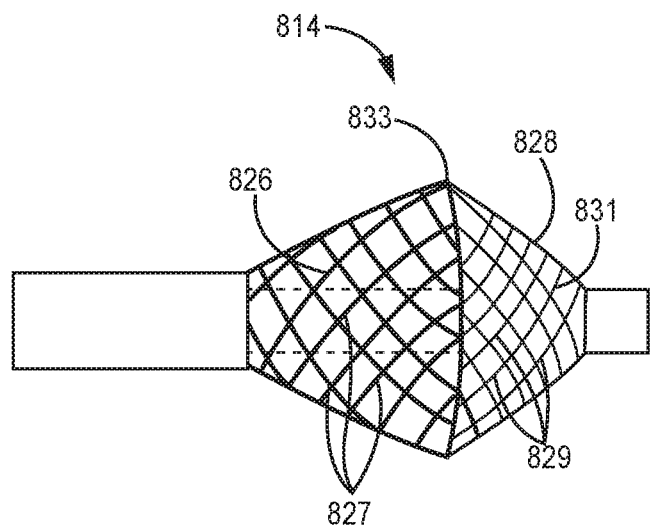
FIG. 15 is a schematic distal end view of another construct of for a filter valve device.

Turning now to FIG. 15, another embodiment of a filter valve 814 substantially as described with respect to a device 300 above, is shown. Filter valve 814 is distinguished in having a thicker braid 827 at its proximal portion 826, and a relatively thinner braid 829 at its distal portion 828. The so-called thinner braid 829 may be the result of a construction of individually thinner braid filaments 831 in a similar braid form as in the proximal portion 826, or a like size braid filament as in the proximal portion but presented in a denser lattice construction in the proximal construction and a wider, less dense lattice construction across the distal portion of the filter valve, or a combination of these two structural design elements. In addition, the filaments of the proximal and distal portions may be otherwise designed to exert differentiated radial force (with greater force at the proximal portion). By way of the example, the filaments of the braid in the proximal portion may be selected to have increased resiliency or spring force, regardless of size or spacing, so as to operate as desired. The proximal and distal portions 826, 828 are preferably demarcated by the circumference about the maximum diameter 833 of the filter valve. The proximal and distal portions 826, 828 may have either homogeneous filter coatings (discussed above with respect to FIGS. 4 and 5) or heterogeneous filter coatings (discussed above with respect to FIGS. 11-13), and common (discussed above with respect to FIGS. 4 and 5) or different braid angles (discussed above with respect to FIG. 14).

Figure 16:
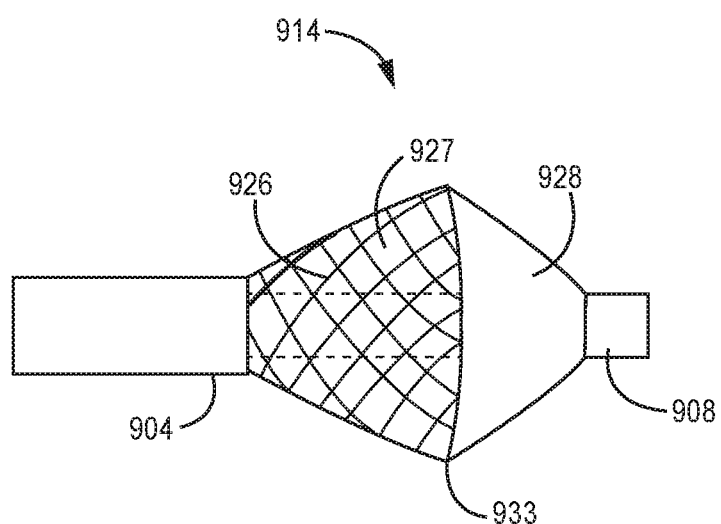
FIG. 16 is a schematic distal end view of yet another construct for a filter valve device.

Referring to FIG. 16, another embodiment of a filter valve 914 for a device as substantially as described with respect to 300 above, is shown. The filter valve 914 includes a proximal filamentary braided portion 926, preferably coated with a polymeric filter material 927, and a distal portion comprising a polymeric filter material 928. The proximal and distal portions 926, 928 are preferably demarcated by the circumference about the maximum diameter 933 of the filter valve. In accord with this embodiment, the distal portion 928 is braidless; i.e., does not include any of the self-expanding filamentary structure. The filter valve 914 may be formed by positioning the filamentary braid for the proximal portion 926 on a mandrel (not shown), and spray coating a porous polymeric membranous material over the proximal braid and also further distally onto the mandrel—where no braid is provided—for construction of the braidless distal portion 928. After curing, the construct is removed from the mandrel. Once the proximal portion 926 of the filter valve 914 is coupled to the outer catheter 904, and the distal portion 928 of the filter valve 914 is coupled to the inner catheter 908, the filter valve has preferred properties. At the distal portion 928, the filter valve 914 is structured substantially similarly to a fabric. That is, when the inner catheter 908 is advanced relative to the outer catheter 904 and the distal portion 928 is placed under tension, the distal portion 928 of the filter valve 914 is strong under tensile force; however, when the inner catheter 908 is retracted relative to the outer catheter 904 and the distal portion 928 is placed under compression, the distal portion of the filter valve is floppy under compression force.

In each of the embodiments of FIGS. 11-16, the distal portion of the filter valve exerts a significantly reduced radial force relative to the proximal portion of the filter valve, which results in optimizing the function of the filter valve as a valve. In forward (downstream) flow of the fluid within the vessel, as the fluid contacts the proximal side of the expanded proximal portion, the fluid flows around filter valve. In distinction, in backward or reflux (upstream) flow of fluid within the vessel as the fluid contact the distal side of the expanded distal portion, the fluid flows into—and not around—the filter valve. In such upstream flow, certain fluids, namely blood, are able to flow through the double layer filter material of the filter valve, while the pores of the filter material are of a sufficiently small size to capture embolic agents and other therapeutic agents of interest.

In any of the embodiments described herein, the components of the valve may be coated to reduce friction in deployment and retraction. The components may also be coated to reduce thrombus formation along the valve or to be compatible with therapeutics, biologics, or embolics. The components may be coated to increase binding of embolization agents so that they are removed from the vessel during retraction.

According to one aspect of the invention, the catheter body and mesh may be separately labeled for easy visualization under fluoroscopy. The catheter body can be labeled by use of any means known in the art; for example, compounding a radio-opaque material into the catheter tubing. The radio-opaque material can be barium sulfate, bismuth subcarbonate or other material. Alternatively or additionally, radio-opaque medium can be compounded into the materials of the braid and the filter. Or, as previously described, one or more of the filaments may be chosen to be made of a radio-opaque material such as platinum iridium.

In each of the embodiments, the inner catheter may be a single lumen or a multi-lumen catheter. Preferably, the catheter has at least one lumen used to deliver the embolization agents, and one or more additional lumen may be provided, if desired, for passage of a guidewire or other devices or to administer fluids, e.g., for flushing the artery after the administration of embolization agents.

The above apparatus and methods have been primarily directed to a system which permits proximal and distal flow of biological fluid (e.g., blood) within a body vessel, and which prevents reflux of an infusate past the valve in a proximal direction. It is appreciated that the valve may also be optimized to reduce blood flow in the distal direction. In any of the embodiments, the radial force of the filter valve can be tuned by adjusting the braid angle. Tuning the radial force allows the blood flow to be reduced by up to more than 50 percent. By way of example, providing a braid angle greater than 130° will significantly reduce blood flow past the valve in the distal direction, with a braid angle of approximately 150° slowing the blood flow by 50 to 60 percent. Other braid angles can provide different reductions in distal blood flow. The reduced distal blood flow can be used in place of a 'wedge' technique, in which distal blood flow is reduced for treatment of brain and spinal arteriovenous malformations. Once the blood flow is slowed by the valve, a glue such as a cyanoacrylic can be applied at the target site.

While the above description has been primarily directed to use of the device for infusing a therapeutic agent, it is appreciated that the device has significant functionality even when delivery of a therapeutic agent is not the primary function. By way of example, the device can be used to retrieve a thrombus and prevent dislodged embolic particles from escaping into the patient's blood. Briefly, a thrombus retrieval device can be passed through the inner catheter 308 to release and retrieve a thrombus. The filter valve 314 operates to prevent the thrombus and spray of embolic particles from passing beyond the filter valve and into the vessel. Then when the thrombus is captured, the thrombus along with any embolic particles can be contained within the filter valve as the filter valve is inverted into the outer catheter for removal from the patient, in a similar method to that discussed above. For such use, the inner catheter may include a single lumen or multiple lumens; i.e., one for the thrombus retrieval device and one or more for additional devices or therapeutic agent infusion.

There have been described and illustrated herein multiple embodiments of devices and methods for reducing or preventing reflux of embolization agents in a vessel. While particular embodiments of the invention have been described, it is not intended that the invention be limited thereto, as it is intended that the invention be as broad in scope as the art will allow and that the specification be read likewise. Thus, while various materials have been listed for the valve filaments, the valve filter, and the inner and outer catheters, it will be appreciated that other materials can be utilized for each of them in each of the various embodiments in combination and without limitation. Also, while the invention has been described with respect to particular arteries of humans, it will be appreciated that the invention can have application to any blood vessel and other vessels, including ducts, of humans and animals. In particular, the apparatus can also be used in treatments of tumors, such as liver, renal or pancreatic carcinomas. Further, the embodiments have been described with respect to their distal ends because their proximal ends can take any of various forms, including forms well known in the art. By way of example only, the proximal end can include two handles with one handle connected to the inner catheter, and another handle connected to the outer catheter. Movement of one handle in a first direction relative to the other handle can be used to extend the filter valve in the non-deployed configuration for advancement to the treatment site, and movement of that handle in an opposite second direction can be used to deploy the filter valve. Depending upon the handle arrangement, filter valve deployment can occur when the handles are moved away from each other or towards each other. As is well known, the handles can be arranged to provide for linear movement relative to each other or rotational movement. If desired, the proximal end of the inner catheter can be provided with hash-marks or other indications at intervals along the catheter so that movement of the handles relative to each other can be visually calibrated and give an indication of the extent to which the valve is opened. It will therefore be appreciated by those skilled in the art that yet other modifications could be made to the provided invention without deviating from its spirit and scope as claimed.

What is claimed is:

1. An endovascular microvalve device for temporary use in a vessel during an intravascular procedure, comprising:
   a) a flexible outer catheter having a proximal end and a distal end;
   b) a flexible inner catheter having a proximal end and a distal end with an orifice, the inner catheter extending through and longitudinally displaceable relative to the outer catheter; and
   c) a filter valve having a proximal end and distal end, the proximal end of the filter valve coupled to the distal end of the outer catheter, and the distal end of the filter valve coupled to the inner catheter adjacent the distal end of the inner catheter, such that longitudinal displacement of the inner catheter relative to the outer catheter moves the filter valve from a non-deployed configuration to a deployed configuration, the filter valve having a proximal portion and distal portion, and a maximum diameter of the filter valve being defined between the proximal and distal portions, the proximal portion exerting an increased radial force relative to the distal portion, and the distal portion comprising a porous polymeric material defining a pore size not exceeding 500 μm wherein:
      once said filter valve is in said deployed state in the vessel, said filter valve is adapted to be dynamically movable depending on a local fluid pressure about said filter valve, such that,
      when the fluid pressure is higher on a proximal side of the filter valve, the filter valve assumes a first configuration with a first maximum diameter smaller than the diameter of the vessel such that fluid flow about the filter valve is permitted, and
      when said fluid pressure is higher on a distal side of the filter valve, the higher fluid pressure causes the filter valve to assume a second configuration with a second maximum diameter relatively larger than the first maximum diameter and in which the filter valve is adapted to contact the vessel wall.

2. An endovascular microvalve device according to claim 1, wherein:
   the proximal portion includes a filamentary braid, and the distal portion is constructed without a filamentary braid.

3. An endovascular microvalve device according to claim 2, wherein:
   the porous polymeric material of the distal portion is a membranous material.

4. An endovascular microvalve device according to claim 3, wherein:
   the proximal portion includes a porous polymeric membranous material.

5. An endovascular microvalve device according to claim 1, wherein:
   each of the proximal and distal portions have a filamentary braid, wherein the filamentary braid of the proximal portion has a different structural property than the filamentary braid of the distal portion.

6. An endovascular microvalve device according to claim 5, wherein:
   wherein the porous polymeric material changes shape and moves with the filamentary braid as fluid pressure conditions about said filter valve change.

7. An endovascular microvalve device according to claim 1, wherein:
   the proximal portion includes a filamentary braid with first filaments, and the distal portion includes a filamentary braid with second filaments, wherein the first filaments have an increased radial spring force relative to the second filaments.

8. An endovascular microvalve device according to claim 1, wherein:
   the proximal portion includes a filamentary braid with first filaments and a polymeric coating, and the distal portion includes a filamentary braid with second filaments, wherein the first filaments and the polymeric coating together have an increased radial spring force relative to the second filaments and the porous polymeric material.

9. An endovascular microvalve device according to claim 1, wherein:
   the filter valve in the deployed configuration forms a substantially oblong spherical or frustoconical shape.

10. An endovascular microvalve device according to claim 1, wherein:
    the distal end of the inner catheter has a first radiopaque marker, the distal end of the outer catheter has a second radiopaque marker, and the inner catheter includes a third radiopaque marker longitudinally offset from the first radiopaque marker, wherein the relative positions of the first, second and third radiopaque marker indicates the configuration of the filter valve.

11. An endovascular microvalve device according to claim 1, wherein:
    the porous polymeric material is homogenous over the filter valve.

12. An endovascular microvalve device according to claim 1, wherein:
    the porous polymeric material is heterogeneously disposed over the filter valve.

13. An endovascular microvalve device according to claim 12, wherein:
    the porous polymeric material has smaller pores at a proximal portion of the filter valve.

14. An endovascular microvalve device according to claim 12, wherein:
    the filter valve further includes a non-porous membrane over a proximal portion of the filter valve.

15. An endovascular microvalve device according to claim 1, wherein:
in a non-deployed configuration, the filter valve includes a distal face that is convex in shape, and in a deployed configuration, the distal face of the filter valve is planar or concave.

16. An endovascular microvalve device according to claim 1, wherein:
in a non-deployed configuration, the filter valve tapers distally over at least 50% of its length, and in a deployed configuration, the distal end of the filter valve has a maximum diameter of the filter valve.

17. An endovascular microvalve device according to claim 1, wherein:
the filter valve includes a braid of filaments having a variable braid angle.

18. An endovascular microvalve device according to claim 17, wherein:
the braid angle is smaller across a proximal portion of the filter valve and larger across a distal portion of the filter valve.

19. An endovascular microvalve device for temporary use in a vessel during an intravascular procedure, comprising:
a) a flexible outer catheter having a proximal end and a distal end;
b) a flexible inner catheter having a proximal end and a distal end with an orifice, the inner catheter extending through and longitudinally displaceable relative to the outer catheter; and
c) a filter valve having a proximal end and distal end, the proximal end of the filter valve coupled to the distal end of the outer catheter, and the distal end of the filter valve coupled to the inner catheter adjacent the distal end of the inner catheter, such that longitudinal displacement of the inner catheter relative to the outer catheter moves the filter valve from a non-deployed configuration to a deployed configuration, the filter valve including,
i) a plurality of elongate first filaments in a braid, each of said first filaments having a diameter of 0.025 mm to 0.127 mm, the first filaments having a proximal end, a distal end, and a length extending therebetween,
the proximal ends secured relative to each other on the outer catheter such that the first filaments define a round configuration between their secured proximal ends on the outer catheter,
the distal ends secured relative to each other on the inner catheter proximal of the orifice, such that the first filaments define a round configuration between their secured distal ends on the inner catheter,
the first filaments along the lengths between the secured proximal and distal ends not bonded to each other such that the first filaments are movable relative to each other, and
the first filaments movable into a collapsed non-deployed configuration relative to each other, and expandable from the non-deployed configuration into a radially-expanded deployed configuration by retraction of the inner catheter relative to the outer catheter, and ii) a filter comprising a polymeric coating on said braided first filaments between said proximal and distal ends of said first filaments, said filter defining a pore size not exceeding 500 μm,
wherein once said filter valve is in said deployed state in the vessel, said filter valve is adapted to be dynamically movable depending on a local fluid pressure about said filter valve, such that
when the fluid pressure is higher on a proximal side of the filter valve, the filter valve assumes a first configuration with a first maximum diameter smaller than the diameter of the vessel such that fluid flow about the filter valve is permitted, and
when said fluid pressure is higher on a distal side of the filter valve, the higher fluid pressure causes the filter valve to assume a second configuration with a second maximum diameter relatively larger than the first maximum diameter and in which the filter valve is adapted to contact the vessel wall, and
wherein the polymeric coating onto the first filaments of the filter valve constrains the polymeric coating to change shape and move with the first filaments as fluid pressure conditions about the filter valve change.

20. An endovascular microvalve device according to claim 19, wherein:
the filter valve in the deployed configuration forms a substantially oblong frustoconical or oblong spherical shape.

21. An endovascular microvalve device according to claim 19, wherein:
the filter is homogenous over the filter valve.

22. An endovascular microvalve device according to claim 19, wherein:
the filter is heterogeneously disposed over the filter valve.

23. An endovascular microvalve device according to claim 22, wherein:
the filter further includes a non-porous membrane over a proximal portion of the filter valve.

24. An endovascular microvalve device according to claim 19, wherein:
the filter has smaller pores at a proximal portion of the filter valve.

25. An endovascular microvalve device according to claim 19, wherein:
in a non-deployed configuration, a distal face of the filter valve is convex, and in a deployed configuration, the face of the filter valve is planar or concave.

26. An endovascular microvalve device according to claim 19, wherein:
in a non-deployed configuration, the filter valve tapers distally over at least 50% of its length, and in a deployed configuration, the distal end of the filter valve has a maximum diameter of the filter valve.

27. An endovascular microvalve device according to claim 19, wherein:
the first filaments in the braid have a variable braid angle.

28. An endovascular microvalve device according to claim 27, wherein:
the braid angle is smaller across a proximal portion of the filter valve and larger across a distal portion of the filter valve.

* * * * *